(12) United States Patent
Komatsu et al.

(10) Patent No.: US 7,858,842 B2
(45) Date of Patent: Dec. 28, 2010

(54) ABSORBENT ARTICLE

(75) Inventors: Shimpei Komatsu, Kagawa (JP); Tatsuya Tamura, Kagawa (JP); Satoshi Mizutani, Mitoyo-gun (JP)

(73) Assignee: Uni-Charm Corporation, Ehime-ken (JP)

( * ) Notice: Subject to any disclaimer, the term of this patent is extended or adjusted under 35 U.S.C. 154(b) by 270 days.

(21) Appl. No.: 11/108,011

(22) Filed: Apr. 14, 2005

(65) Prior Publication Data

US 2005/0256475 A1  Nov. 17, 2005

(30) Foreign Application Priority Data

Apr. 27, 2004  (JP) .............................. 2004-131747

(51) Int. Cl.
*A61F 13/15* (2006.01)

(52) U.S. Cl. ..................... 604/378; 604/372; 604/383; 604/385.08

(58) Field of Classification Search ................. 604/372, 604/378, 383, 385.08, 387
See application file for complete search history.

(56) References Cited

U.S. PATENT DOCUMENTS

| | | | |
|---|---|---|---|
| 4,761,322 A | | 8/1988 | Raley |
| 4,806,411 A | * | 2/1989 | Mattingly et al. ........... 428/139 |
| 5,078,710 A | * | 1/1992 | Suda et al. ................... 604/383 |
| 5,387,209 A | * | 2/1995 | Yamamoto et al. .......... 604/384 |
| 5,591,510 A | * | 1/1997 | Junker et al. ................ 428/132 |
| 5,614,283 A | * | 3/1997 | Potnis et al. ................ 428/131 |
| 6,303,208 B1 | * | 10/2001 | Pelkie ........................ 428/138 |
| 6,794,556 B2 | * | 9/2004 | Shibata et al. .............. 604/372 |
| 2002/0133132 A1 | | 9/2002 | Copat et al. |
| 2003/0195487 A1 | * | 10/2003 | Thomas ................. 604/385.01 |

FOREIGN PATENT DOCUMENTS

| | | |
|---|---|---|
| EP | 0 358 031 A | 3/1990 |
| EP | 0 489 205 A | 6/1992 |
| EP | 0 523 719 A | 1/1993 |
| EP | 0 545 423 A | 6/1993 |

(Continued)

OTHER PUBLICATIONS

European Search Report for EP 05 00 7614 dated Sep. 6, 2005.

(Continued)

*Primary Examiner*—Tatyana Zalukaeva
*Assistant Examiner*—Lynne Anderson
(74) *Attorney, Agent, or Firm*—Morrison & Foerster LLP

(57) ABSTRACT

Disclosed is an absorbent article including a liquid absorbent layer for absorption and retention of liquid and a liquid passage layer located on a liquid-receiving side of the liquid absorbent layer. The liquid passage layer includes a first passage layer and a second passage layer disposed between the first passage layer and the liquid absorbent layer. The first passage layer and the second passage layer are resin films formed with a plurality of liquid passage apertures. The individual liquid passage apertures are defined by a peripheral wall projecting toward the liquid absorbent layer to provide the first passage layer and the second passage layer with thicknesses greater than a thickness of the resin film itself. Under a load in a thickness direction, the second passage layer has a greater compressibility than the first passage layer.

12 Claims, 6 Drawing Sheets

| | FOREIGN PATENT DOCUMENTS | | |
|---|---|---|---|
| EP | 0 953 324 A | 11/1999 |
| EP | 1 208 828 A | 5/2002 |
| EP | 1 275 361 A | 1/2003 |
| JP | 04-024263 | 1/1992 |
| JP | 9-507408 | 7/1997 |
| JP | 10-272152 A | 10/1998 |
| JP | 11-513904 | 11/1999 |
| JP | 2002-253610 A | 9/2002 |
| WO | WO-03/048436 A | 6/2003 |

OTHER PUBLICATIONS

Patent Abstracts of Japan for 10272152 published on Oct. 13, 1998.

* cited by examiner

ABSORBENT ARTICLE

BACKGROUND OF THE INVENTION

1. Field of the Invention

The present invention relates to an absorbent article to be worn on the human body to absorb liquid and more particularly to an absorbent article suitable for use as a sanitary napkin.

2. Description of the Related Art

Absorbent articles such as sanitary napkins are typically constructed to include a liquid absorbent layer which contains fluff pulp and whose skin-side surface is covered with a liquid passage layer (topsheet). This liquid passage layer allows rapid transfer of an applied liquid into the liquid absorbent layer and is preferably constructed to prevent a liquid applied to the liquid absorbent layer from returning to the skin-side surface of the absorbent article.

Japanese Unexamined Patent Publication No. H04-24263 discloses a liquid passage layer which is constructed by stacking two nonwoven fabrics. Since the liquid passage layer is constructed of nonwoven fabrics having a lot of voids therein, a liquid applied to the skin-side surface of the absorbent article is allowed to easily reach the liquid absorbent layer through the voids. The nonwoven fabric is also intended to provide an improved feeling when in contact with the human bodies.

Japanese Unexamined Patent Publication No. H09-507408 discloses a liquid passage layer which is constructed of a resin film having a large number of liquid passage apertures and a nonwoven fabric disposed beneath the resin film. In the liquid passage layer, a liquid applied to the skin-side surface of the resin film passes through the liquid passage apertures of the resin film and then passes through the nonwoven fabric for absorption into the liquid absorbent layer. The nonwoven fabric, which is disposed between the resin film and the liquid absorbent layer to put distance therebetween, effectively prevents a liquid absorbed in the liquid absorbent layer from returning to the skin-side surface of the resin film. In addition, from whitening the resin film, it is also expected that the color of liquid absorbed in the liquid absorbent layer will be less noticeable in surface view of the absorbent article.

Japanese Unexamined Patent Publication No. H11-513904 discloses a liquid passage layer which is constructed by stacking two resin films. The two resin films are individually formed with a large number of liquid passage apertures, but the liquid passage apertures in the upper resin film (the resin film located on the skin-side surface of the liquid passage layer) have a larger individual open area than the liquid passage apertures in the lower resin film (the resin film located on the garment-side surface of the liquid passage layer) and the upper resin film has a larger percent open area due to the liquid passage apertures than the lower resin film. The upper resin film, which is less resistant to liquid passage, allows rapid passage of an applied liquid, while the lower resin film allows gradual passage of a liquid introduced into the space between the upper resin film and the lower resin film for absorption into the liquid absorbent layer. In the liquid passage layer, the resistance to liquid passage is higher in a direction from the liquid absorbent layer to the skin-side surface of the liquid passage layer than in a direction from the skin-side surface of the liquid passage layer to the liquid absorbent layer, so that a liquid absorbed in the liquid absorbent layer is less apt to return to the skin-side surface of the liquid passage layer.

In the case where the liquid passage layer is constructed by stacking two nonwoven fabrics, as described in Patent Publication No. H04-24263, resistance to liquid passage in the direction from the skin-side surface of the liquid passage layer to the liquid absorbent layer is almost equal to that in the direction from the liquid absorbent layer to the skin-side surface of the liquid passage layer. Therefore, when body pressure is exerted on the skin-side surface of the liquid passage layer, a liquid absorbed in the liquid absorbent layer easily passes through the nonwoven fabrics to return to the skin-side surface of the liquid passage layer. In addition, while the nonwoven fabrics are permeable to liquid, liquid is apt to be retained inside them and remain behind. Inside the nonwoven fabrics, more specifically, voids of various sizes are defined between fibers. While a liquid given to large voids easily passes through them under gravitation to migrate toward the liquid absorbent layer, a liquid introduced into small voids is finely divided to have a small weight, so that it tends to be retained in the small voids without migrating toward the liquid absorbent layer. In the case where the liquid passage layer consists essentially of nonwoven fabrics, because liquid is apt to return to the skin-side surface of the liquid passage layer from the liquid absorbent layer and is also apt to remain inside the liquid passage layer, as set forth above, the wearer's skin tends to be wetted to cause discomfort.

The liquid passage layer disclosed in Patent Publication No. H09-507408 is more effective in preventing wetting of the skin-side surface of the liquid passage layer than that disclosed in Patent Publication No. H04-24263, because a resin film having a large number of liquid passage apertures is laid on a nonwoven fabric. However, the nonwoven fabric located beneath the resin film is apt to retain liquid and cannot easily recover to its original state from a compressed state because when body pressure is exerted on the nonwoven fabric in a liquid retaining state, its elasticity decreases. Therefore, the distance between the liquid absorbent layer and the resin film becomes difficult to maintain and a liquid absorbed in the liquid absorbent layer easily oozes out to appear on the resin film and come into contact with the wearer's skin.

On the other hand, the liquid passage layer disclosed in Patent Publication No. H11-513904 is improved in resistance to liquid passage in the direction from the liquid absorbent layer to the skin-side surface of the liquid passage layer by stacking two resin films having a large number of liquid passage apertures. However, since the liquid passage apertures in the upper resin film have a large individual open area and the upper resin film has a large percent open area due to the liquid passage apertures, the upper resin film is apt to be compressed when subjected to body pressure. When the upper resin film, which comes into direct contact with the wearer's skin, is compressed, relatively stiff aperture edges around the liquid passage apertures tend to irritate the skin to cause pain or itching. At this time, moreover, since both the individual open area and the percent open area decrease in the upper resin film, the resistance to liquid passage is increased, so that an applied liquid such as menstrual blood is apt to remain on the skin-side surface of the liquid passage layer and adhere to the wearer's skin.

SUMMARY OF THE INVENTION

The present invention has been developed to solve the problems in the prior art set forth above and has an object to provide an absorbent article which facilitates liquid transfer in a direction from its skin-side surface to a liquid absorbent layer but is resistant to liquid return in the opposite direction and is also less irritating to the wearer's body to give a pleasant feeling.

According to the present invention, there is provided an absorbent article comprising a liquid absorbent layer for absorption and retention of liquid and a liquid passage layer located on a liquid-receiving side of the liquid absorbent layer, the liquid passage layer including a first passage layer and a second passage layer disposed between the first passage layer and the liquid absorbent layer, the first passage layer and the second passage layer being resin films formed with a plurality of liquid passage apertures, the individual liquid passage apertures being defined by a peripheral wall projecting toward the liquid absorbent layer to provide the first passage layer and the second passage layer with thicknesses greater than a thickness of the resin film itself, wherein under a load in a thickness direction, the second passage layer has a greater compressibility than the first passage layer.

When the absorbent article is subjected to body pressure, the second passage layer is allowed to be compressed more easily than the first passage layer. Therefore, the shape of the liquid passage apertures can be easily maintained in the first passage layer so as not to produce an unpleasant feeling or irritation due to compression. On the other hand, compression of the second passage layer relieves the body pressure to have a soft touch. Moreover, since the individual open area of the liquid passage apertures does not decrease very much in the first passage layer, a liquid applied to the first passage layer easily passes through it to reach the second passage layer, thereby preventing residual liquid on the skin-side surface of the absorbent article.

Under a load in a thickness direction, preferably, the second passage layer has a greater thickness variation than the first passage layer.

When the individual first and second passage layers are under a load in a thickness direction, preferably, the first passage layer has a compression workload equal to or greater than 0.1 N·m/m$^2$ and the second passage layer has a greater compression workload than the first passage layer so as to provide a resilient, soft feeling under body pressure.

When the individual first and second passage layers are under a load in a thickness direction, preferably, the second passage layer has a greater reduction in open area than the first passage layer. In the case, liquid-permeability of the first passage layer can be maintained even after the absorbent article is subjected to body pressure.

According to the present invention, as set forth above, the resistance to liquid passage is higher in a direction from the liquid absorbent layer to the skin-side surface of the liquid passage layer than in a direction from the skin-side surface of the liquid passage layer to the liquid absorbent layer, so that liquid return in the direction from the liquid absorbent layer to the skin-side surface of the liquid passage layer can be easily prevented. In addition, since the two resin films are stacked, the color of liquid absorbed in the liquid absorbent layer becomes less noticeable. Moreover, the liquid passage layer can provide a resilient, soft feeling under body pressure. Furthermore, since fine irregularities due to difference in stiffness caused by collapse of the liquid passage apertures do not come into direct contact with the skin, the liquid passage layer becomes less irritating to the skin. Still furthermore, liquid can be prevented from remaining on the skin-side surface of the liquid passage layer.

DESCRIPTION OF THE PREFERRED EMBODIMENT

It should be noted that the sanitary napkin, as well as its individual components, has two major surfaces: of which one surface intended to be worn toward the wearer's crotch is referred to as "skin-side surface", while the other surface is referred to as "garment-side surface".

Figure 1:
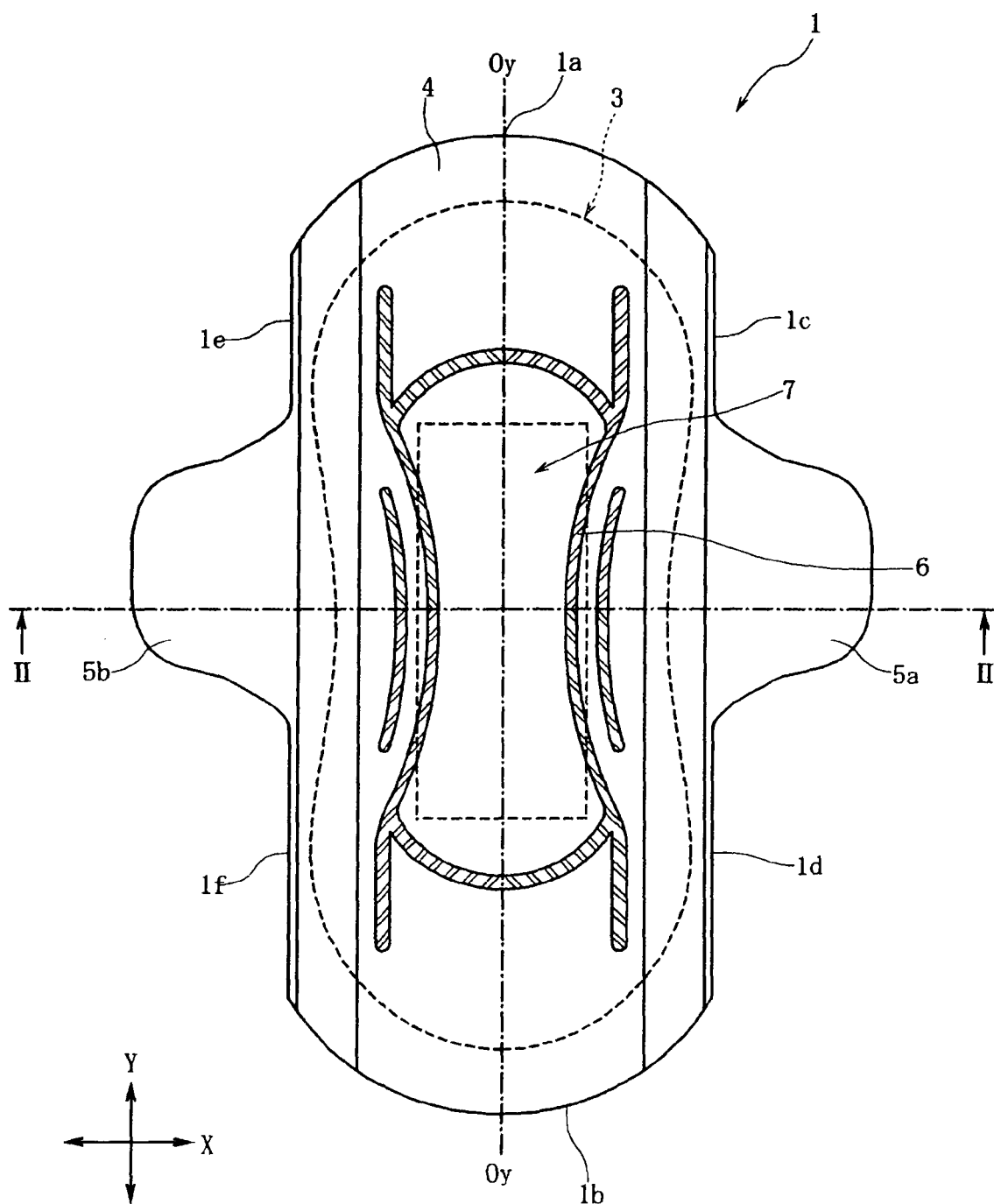
FIG. 1 is a plan view of a sanitary napkin as an absorbent article according to one embodiment of the present invention.
Figure 2:
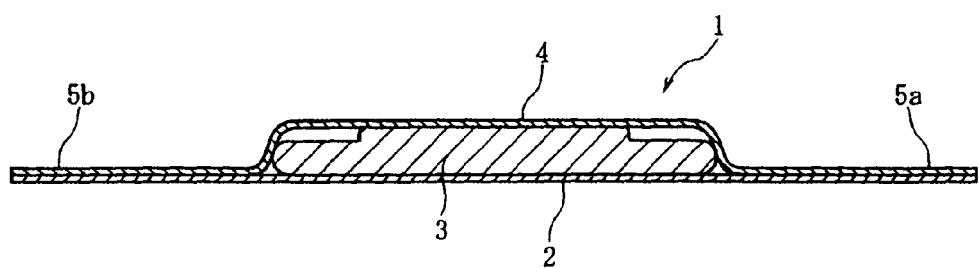
FIG. 2 is a sectional view taken along line II-II of FIG. 1.
Figure 3:
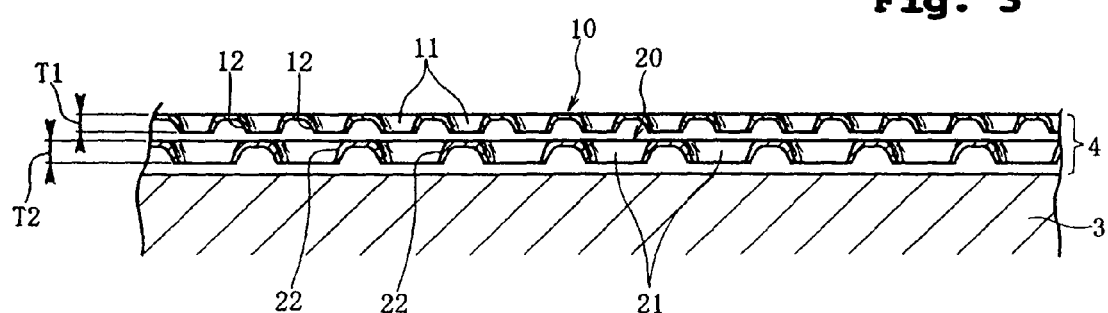
FIG. 3 is an enlarged sectional view showing a liquid passage layer under no pressure.
Figure 4:
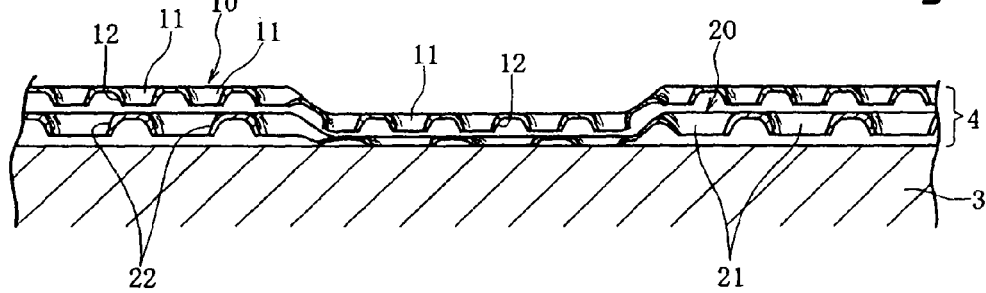
FIG. 4 is an enlarged sectional view showing a liquid passage layer under a pressure.

FIG. 1 is a plan view showing the skin-side surface of a sanitary napkin 1 as an absorbent article according to a first embodiment of the present invention, FIG. 2 is a sectional view taken along line II-II of FIG. 1, and FIGS. 3 and 4 are partial enlarged views of FIG. 2.

As shown in FIG. 2, the sanitary napkin 1 has a liquid-blocking backsheet 2, a liquid absorbent layer 3 disposed on the backsheet 2, and a liquid passage layer (topsheet) 4 covering the liquid absorbent layer 3. The backsheet 2 is located on the garment-side surface to be directed toward a garment such as shorts, while the liquid passage layer 4 is located on the skin-side surface to be directed toward the wearer's body. As shown in FIG. 1, the backsheet 2 and the liquid passage layer 4 are of a larger area than the liquid absorbent layer 3 and bonded together in a peripheral region outside the liquid absorbent layer 3 through a hot-melt type adhesive. The liquid absorbent layer 3 and the backsheet 2 are also bonded together through a hot-melt type adhesive, while the liquid absorbent layer 3 and the liquid passage layer 4 are bonded together through a hot-melt type adhesive applied in such an amount as not to interfere with liquid transfer.

As shown in FIG. 1, the sanitary napkin 1 has front and rear edges 1a and 1b that are arcuately curved to project forward and rearward, respectively. Forward and rearward right edges 1c and 1d extend linearly in a longitudinal direction (Y-direction). Between the forward and rearward right edges 1c and 1d, the backsheet 2 and the liquid passage layer 4 project rightward to provide a wing 5a. Likewise, forward and rearward left edges 1e and 1f extend linearly in the longitudinal direction. Between the forward and rearward left edges 1e and 1f, the backsheet 2 and the liquid passage layer 4 project leftward to provide a wing 5b.

In the skin-side surface of the sanitary napkin 1, as shown in FIG. 1, there are formed compressed grooves 6 where the liquid absorbent layer 3 is compressed together with the liquid passage layer 4. The compressed grooves 6 are formed in a pattern of FIG. 1, so that a main absorbent region 7 enclosed by the compressed grooves 6 is formed centrally of the skin-side surface of the sanitary napkin 1.

As shown in FIG. 3 on an enlarged scale, the liquid passage layer 4 is composed of a first passage layer 10 for facing the wearer's skin and a second passage layer 20 located closer to the liquid absorbent layer 3. The first passage layer 10 is a resin film having a large number of liquid passage apertures 11, while the second passage layer 20 is a resin film having a large number of liquid passage apertures 21. The first passage layer 10 and the second passage layer 20 are bonded together through a hot-melt type adhesive applied in such an amount as not to interfere with liquid transfer.

In FIG. 1, the first passage layer 10 has the same contour as the sanitary napkin 1 and the liquid passage apertures 11 are distributed at least in the main absorbent region 7 enclosed by the compressed grooves 6. The second passage layer 20 is disposed beneath the first passage layer 10 at least in the main absorbent region 7 and the liquid passage apertures 21 are distributed at least in the main absorbent region 7. Here, the second passage layer 20 may have the same contour as the sanitary napkin 1, like the first passage layer 10. The liquid passage apertures 11, 21 may be distributed, for example, over the region where the liquid absorbent layer 3 is present.

In the sanitary napkin 1, the liquid passage layer 4 composed of the first and second passage layers 10 and 20 serves as a topsheet, so that the first passage layer 10 appears on the skin-side surface of the sanitary napkin 1 for coming into direct contact with the wearer's skin. If desired, a liquid-permeable thin nonwoven fabric or the like, which is substantially incapable of retaining liquid, may be laid on the skin-side surface of the first passage layer 10. It is also possible to put distance between the second passage layer 20 and the liquid absorbent layer 3 by disposing therebetween a nonwoven fabric, e.g., a through-air bonded nonwoven fabric.

The first passage layer 10 and the second passage layer 20 may be resin films made of LDPE (low-density polyethylene), LLDPE (linear low-density polyethylene), MDPE (medium-density polyethylene) or HDPE (high-density polyethylene) or multi-layered resin films thereof. The films may be made of a foamed resin. The resin films are whitened by incorporating with the resin material a whitening filler such as titanium oxide. When such white resin films are used, the absorbent article looks clean and the color of menstrual blood absorbed in the liquid absorbent layer 3 becomes less noticeable.

It should be noted that the term "resin film" as used herein for the first and second passage layers 10, 20 includes an apertured nonwoven fabric (e.g., meltblown or spunbonded nonwoven fabric) whose fibers are fusion-bonded together or which is treated to be water-repellent so that liquid cannot pass through it except for the liquid passage apertures 11, 21.

In the first passage layer 10, the individual liquid passage apertures 11 are defined by a peripheral wall 12 projecting toward the second passage layer 20, so that the first passage layer 10 has an overall thickness T1 which is greater than the thickness of the resin film itself used for the first passage layer 10. Also in the second passage layer 20, the individual liquid passage apertures 21 are defined by a peripheral wall 22 projecting toward the liquid absorbent layer 3, so that the second passage layer 20 has an overall thickness T2 which is greater than the thickness of the resin film itself used for the second passage layer 20.

When the overlap of the first passage layer 10 and the second passage layer 20 is put under a load in the thickness direction, the peripheral wall 22 of the second passage layer 20 is easy to crush, while the peripheral wall 12 of the first passage layer 10 is difficult to crush. That is, when an equal pressure is individually applied to the first passage layer 10 and the second passage layer 20, the second passage layer 20 is allowed to be compressed more easily than the first passage layer 10.

FIG. 4 shows a state where a given area of the skin-side surface of the sanitary napkin 1 is vertically pushed by a finger or the like. Here, the peripheral walls 22 of the liquid passage apertures 21 are crushed to decrease the overall thickness T2 of the second passage layer 20. On the other hand, the overall thickness T1 of the first passage layer 10 is hardly decreased because the peripheral walls 12 of the liquid passage apertures 11 are resistant to crushing as compared with the peripheral walls 22 of the liquid passage apertures 21. Thus, crushing of the peripheral walls 22 in the second passage layer 20 leads to depression of the skin-side surface of the liquid passage layer 4. The liquid passage layer 4 has a cushiony feeling because the crushed peripheral walls 22 produce a resilient force against the pressure.

When the peripheral walls 22 in the second passage layer 20 are crushed, furthermore, the second passage layer 20 is raised or stiffened around the liquid passage apertures 21 due to the crushed peripheral walls 22, which results in fine irregularities. On the second passage layer 20, however, located is the first passage layer 10 whose peripheral walls 12 are maintained in a three-dimensional shape without being totally crushed. Therefore, even when a female genitalia is pressed against and slid on the liquid passage layer 4 during walking or sitting, the fine irregularities of the second passage layer 20 are hardly felt.

When a liquid such as menstrual blood is applied to the skin-side surface of the sanitary napkin, it passes through the liquid passage apertures 11 of the first passage layer 10 and then through the liquid passage apertures 21 of the second passage layer 20 and is then absorbed by the liquid absorbent layer 3. Here, even if the liquid passage layer 4 is compressed by body pressure as shown in FIG. 4, an applied liquid can rapidly pass through the liquid passage apertures 11 of the first passage layer 10, whose peripheral walls 12 are resistant to crushing, to reach the space between the first passage layer 10 and the second passage layer 20. On the other hand, the liquid passage apertures 21 of the second passage layer 20 are narrowed by crushing of the peripheral walls 22, but the liquid having reached the spaced between the first passage layer 10 and the second passage layer 20 is still allowed to gradually permeate through the liquid absorbent layer 3 because it can pass through the narrowed liquid passage apertures 21 by hydrophilic power of the liquid absorbent layer 3. If the body pressure is temporarily relieved, the peripheral walls 22 of the second passage layer 20 can be immediately restored to their original three-dimensional shape to thereby enable rapid liquid transfer into the liquid absorbent layer 3.

The downwardly projecting peripheral walls 12, 22 are effective in preventing liquid from returning to the skin-side surface of the sanitary napkin 1. More specifically, a liquid absorbed in the liquid absorbent layer 3 cannot easily pass through the second passage layer 20, and a liquid remaining in the space between the first passage layer 10 and the second passage layer 20 cannot easily pass through the first passage layer 10.

In order to have the foregoing functions, it is required that the second passage layer 20 is allowed to be compressed more easily than the first passage layer 10 and that when subjected to a pressure in the thickness direction, both the first passage layer 10 and the second passage layer 20 have a certain compression distance and resist compression to some extent.

As will be described hereinbelow, the ease of compression can be expressed by compressibility under pressure and thickness variation under pressure.

(1) Compressibility

The first passage layer 10 and the second passage layer 20 are individually mounted on a flat and rigid measurement table for measurement of total thickness t0 under no pressure and total thickness t50 under a pressure of 4900 Pa (50 g/cm$^2$), where the total thickness means the distance from the skin-side surface of the layer 10/20 to the lower end of the peripheral walls 11/22. The compressibility is expressed by $\{(t0-t50)/t0\}$.

By setting the compressibility of the second passage layer 20 greater than that of the first passage layer 10, the second passage layer 20 can be compressed more easily than the first passage layer 10.

(2) Thickness Variation

The thickness variation is expressed by (t0-t50) which is an absolute dimension (mm). The thickness variation of the second passage layer 20 is preferably greater than that of the first passage layer 10 so as to widely spread a stress caused by compression of the second passage layer 20. If the stress is widely spread, the resilient force against compression feels weak and the liquid passage layer 4 feels soft.

Next, the degree of resistance to compression can be determined by compression workload WC.

(3) Compression Workload WC

Figure 10:
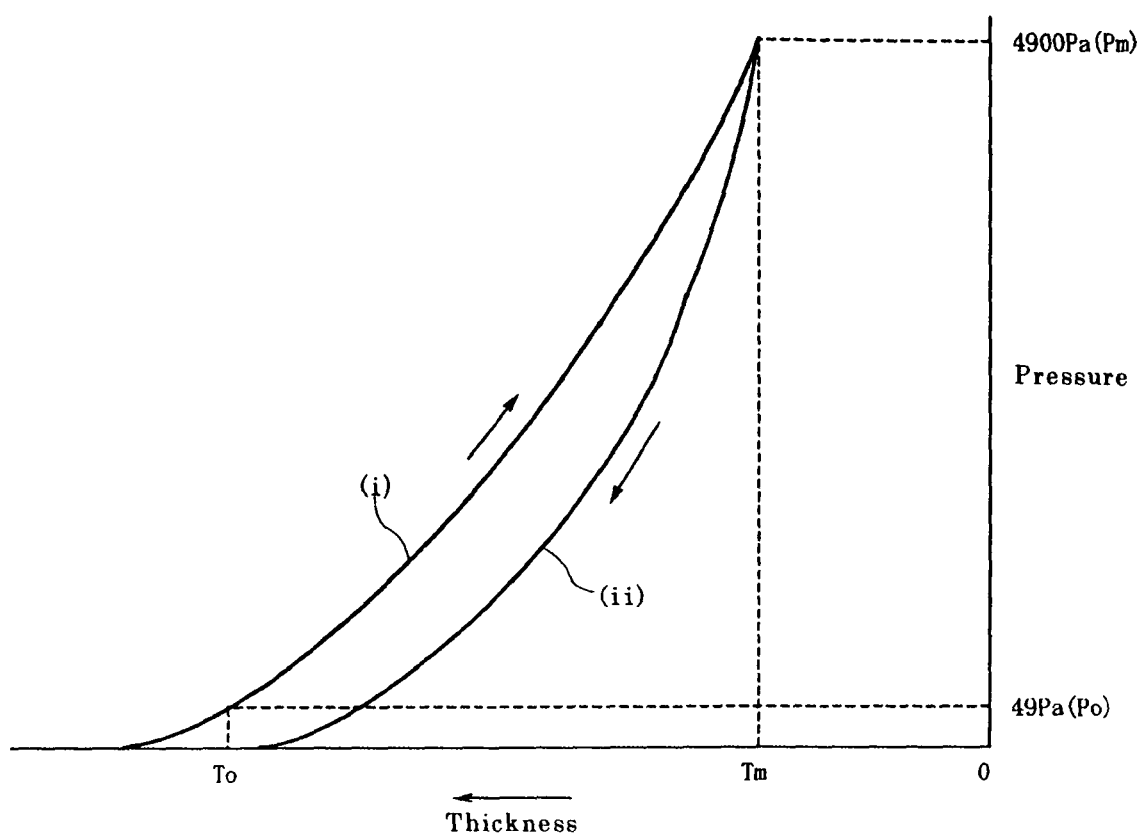
FIG. 10 is a diagram for explanation of compression workload.

Compression properties are measured by using an automatic compression tester "KES FB3-AUTO-A" manufactured by KATO-TECH CO., LTD. FIG. 10 shows a diagram obtained from the measurement.

The first and second passage layers 10, 20 are individually mounted on the automatic compression tester as a sample. An initial pressure P0=49 Pa (0.5 g/cm$^2$) is vertically applied to the sample with a 2 cm$^2$ circular pressing plate for measurement of initial thickness T0. Then, the pressure is linearly increased at a compression rate of 50 sec/mm from the initial pressure P0 to a pressure Pm=4900 Pa (50 g/cm$^2$). The thickness of the sample as measured under the pressure Pm is indicated by Tm.

Compression workload WC is expressed by a value (N·m/m$^2$) of definite integral between T0 and Tm with respect to a curve (i) in FIG. 10, i.e., WC=∫P·dT (P indicates pressure; T indicates thickness). Compressive recovery workload WC' is expressed by a value (N·m/m$^2$) of similar definite integral with respect to a curve (ii) where the pressure varies from Pm to P0. Compressive recovery (RC) is obtained by WC'/WC× 100(%).

The compression workload WC increases with thickness and also increases with resistance to compression. If the compression workload WC is less than 0.1 (N·m/m$^2$), a sample may be weak in resistance to compression or may be too thin to have a significant thickness variation.

In both the first passage layer 10 and the second passage layer 20, the compression workload WC is preferably equal to or greater than 0.1 (N·m/m$^2$). In order to provide a suitable cushiony feeling, furthermore, the compression workload WC of the second passage layer 20 is preferably greater than that of the first passage layer 10.

Next, when the first and second passage layers 10, 20 are under a load, the reduction in open area is preferably greater in the second passage layer 20 than in the first passage layer 10.

(4) Percent Open Area and Reduction in Open Area

Percent open area of an apertured resin film is expressed by {total of minimum open areas of individual apertures within a unit area of an apertured region/said unit area}×100(%).

Reduction in open area of the individual first and second passage layers 10, 20 is expressed by a value obtained by subtracting a percent open area under a given load (for example, 4900 Pa) from a percent open area under no load.

Preferably, the second passage layer 20 has a greater reduction in open area than the first passage layer 10. In this case, even if the individual open area of the liquid passage apertures 21 in the second passage layer 20 decreases under a pressure as shown in FIG. 4, the individual open area of the liquid passage apertures 11 in the first passage layer 10 can remain large enough to allow a liquid applied to the skin-side surface of the liquid passage layer 4 to transfer to the space between the first passage layer 10 and the second passage layer 20 through the liquid passage apertures 11.

In order that the second passage layer 20 may have a greater compressibility, a greater thickness variation and a greater reduction in open area than the first passage layer 10 and that the compression workload WC may be equal to or greater than 0.1 (N·m/m$^2$), the first and second passage layers 10, 20 may be embodies in various ways.

For example, the percent open area of the second passage layer 20 due to the liquid passage apertures 21 may be greater than the percent open area of the first passage layer 10 due to the liquid passage apertures 11. When the resin films used for the first and second passage layers 10, 20 are of a similar thickness, the second passage layer 20 may have a greater compressibility and so on than the first passage layer 10 by making greater the percent open area of the second passage layer 20.

Here, the percent open area of the first passage layer 10 and the percent open area of the second passage layer 20 are both preferably in the range of 5 to 60%, more preferably in the range of 10 to 30%. Individual minimum diameters of the liquid passage apertures 11, 21 are preferably in the range of 0.2 to 3.0 mm, more preferably in the range of 0.3 to 1.5 mm.

The first and second passage layers 10, 20 may also be made different in compressibility and so on by varying the individual open area, the spacing or the arrangement pattern of the liquid passage apertures. For example, even if the resin films used for the first and second passage layers 10, 20 are of a similar thickness and the first and second passage layers 10, 20 are of a similar or identical percent open area, the second passage layer 20 may have a greater compressibility and so on than the first passage layer 10 by making the individual open area of the liquid passage apertures 21 in the second passage layer 20 greater than the individual open area of the liquid passage apertures 11 in the first passage layer 10.

In an alternative, the second passage layer 20 may have a greater compressibility and so on than the first passage layer 10 by making the spacing of the liquid passage apertures 21 in the second passage layer 20 greater than the spacing of the liquid passage apertures 11 in the first passage layer 10.

In another alternative, the second passage layer 20 may have a greater compressibility and so on than the first passage layer 10 by making the thickness of the resin film used for second passage layer 20 smaller than the thickness of the resin film used for the first passage layer 10. In this case, the percent open area of the first passage layer 10 may be greater than the percent open area of the second passage layer 20.

In still another alternative, a resin material used for the second passage layer 20 may be softer than a resin material used for the first passage layer 10. For example, even if the thickness T1 of the first passage layer 10 is equal to the thickness T2 of the second passage layer 20 and the first and second passage layers 10, 20 are of an identical percent open area, the second passage layer 20 may have a greater compressibility and so on than the first passage layer 10 by making the first passage layer 10 of HDPE or MDPE and the second passage layer 20 of LLDPE or LDPE.

The compressibility and so on may also be adjusted by varying the shape of the peripheral walls of the liquid passage apertures.

Figure 5:
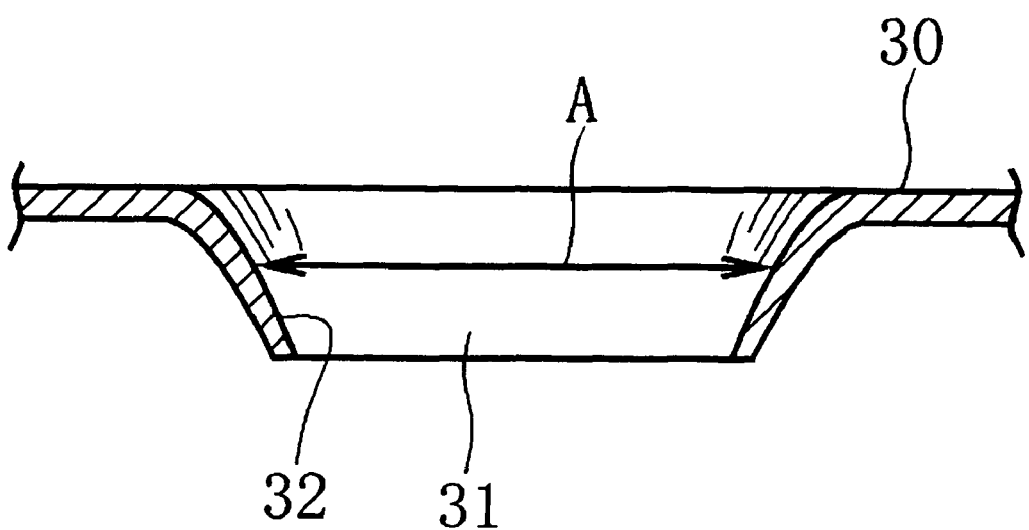
FIG. 5 is an enlarged sectional view showing a structure of a liquid passage aperture.

FIG. 5 shows a liquid passage aperture 31 formed in a resin film 30 and having the same shape as the liquid passage apertures 11 in the first passage layer 10 and the liquid passage apertures 21 in the second passage layer 20. In this embodiment, a peripheral wall 32 is tapered to gradually decrease the sectional area (indicated by A) toward the liquid absorbent layer 3.

Figure 6A:
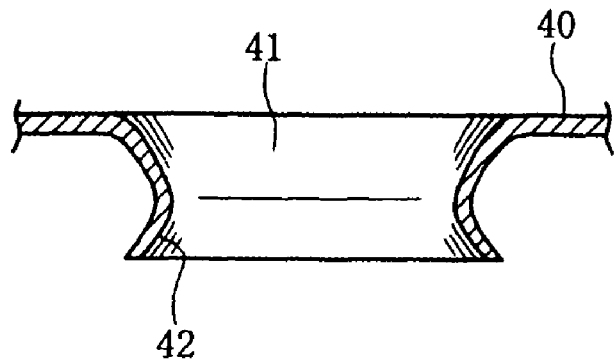
FIGS. 6(A), 6(B), 6(C) and 6(D) are enlarged sectional views showing different shapes of liquid passage apertures.

FIG. 6(A) shows a liquid passage aperture 41 formed in a resin film 40. A peripheral wall 42 is narrowed midway in the thickness direction so that the sectional area becomes smallest midway in the thickness direction.

Figure 6B:
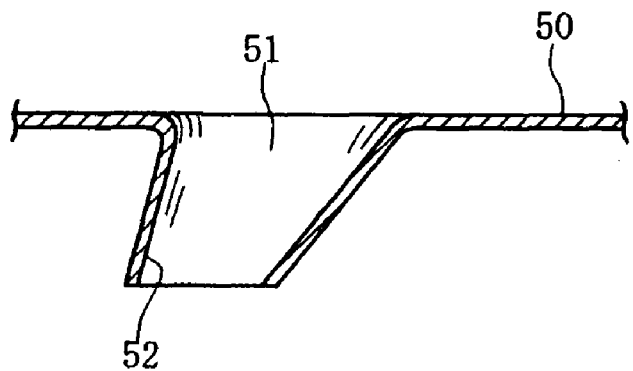

FIG. 6(B) shows a liquid passage aperture 51 formed in a resin film 50. A peripheral wall 52 is tapered to gradually decrease the sectional area toward the liquid absorbent layer 3 with aperture axis extending obliquely downward.

Figure 6C:
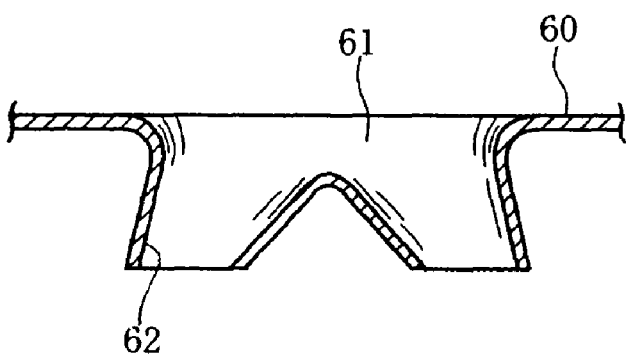

FIG. 6(C) shows a liquid passage aperture 61 formed in a resin film 60 and bifurcated on the way to the liquid absorbent layer 3. Individual channels are tapered to gradually decrease the sectional area toward the liquid absorbent layer 3. In short, a peripheral wall 62 is bifurcated and tapered.

Figure 6D:
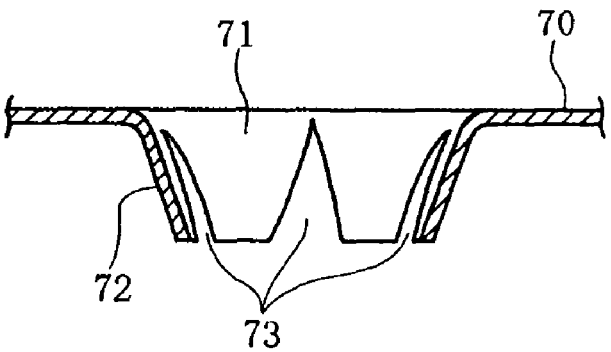

FIG. 6(D) shows a liquid passage aperture 71 formed in a resin film 70. A peripheral wall 72 basically has the same tapered shape as the peripheral wall 32 of FIG. 5 but is formed with a single or a plurality of cuts 73.

The peripheral wall 42 of FIG. 6(A) can be crushed easily as compared with the peripheral wall 32 of FIG. 5. Moreover, crushing of the peripheral walls becomes easier in the order, FIG. 6(B), FIG. 6(C), FIG. 6(D). Therefore, the second passage layer 20 may have a greater compressibility and a greater thickness variation than the first passage layer 10 by forming the first passage layer 10 in the structure shown in FIG. 5 and forming the second passage layer 20 in the structure shown in any one of FIGS. 6(A), 6(B), 6(C) and 6(D).

Example

Apertured Resin Film

Figure 7:
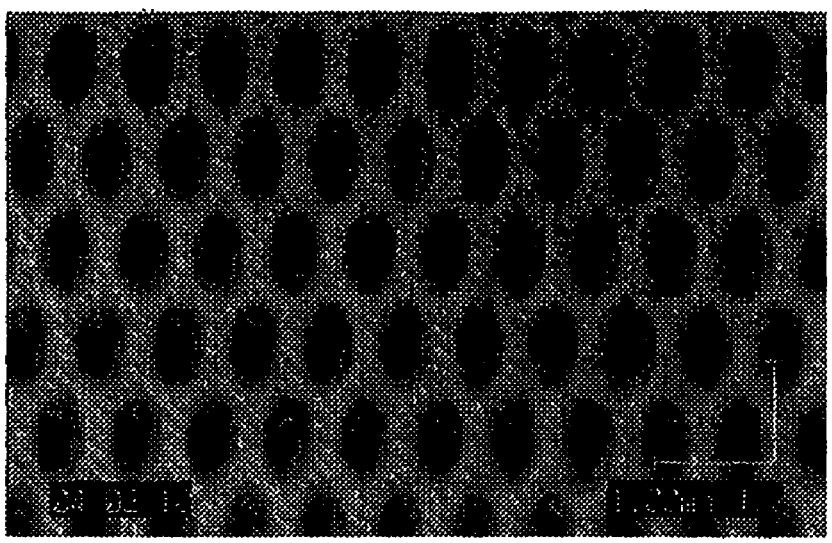
FIG. 7 is a close-up picture of an example of an apertured film.
Figure 8:
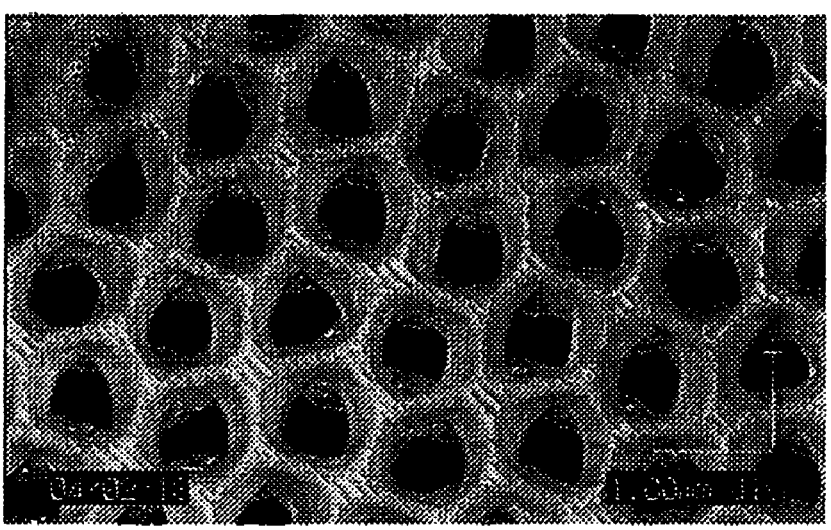
FIG. 8 is a close-up picture of an example of an apertured film.
Figure 9:
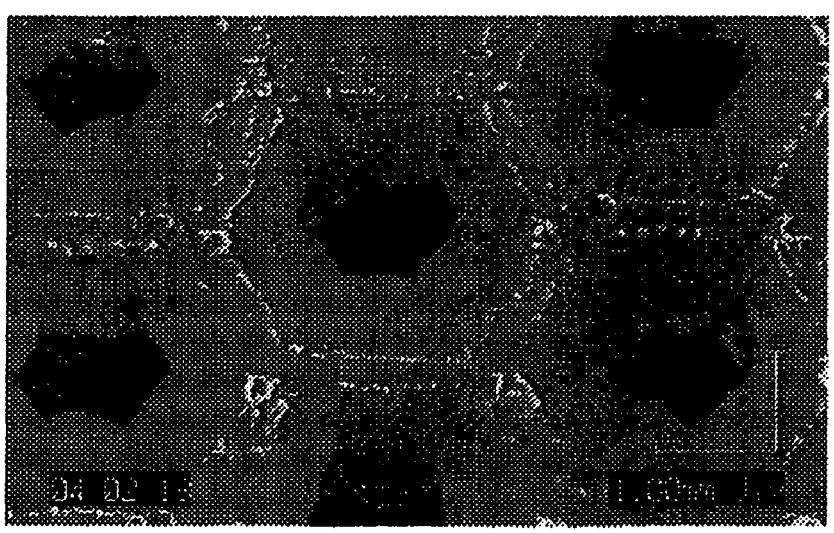
FIG. 9 is a close-up picture of an example of an apertured film.

Various properties were measured for apertured films shown in FIGS. 7, 8 and 9. The basis weight of the individual apertured films, the opening diameter (maximum opening size/minimum opening size) of the individual liquid passage apertures and the percent open area are shown in Table 1.

For the individual apertured films, the initial thickness T0 (mm) and the thickness Tm (mm) under load were measured by using the automatic compression tester "KES FB3-AUTO-A" manufactured by KATO-TECH CO., LTD. Also measured were the compression workload WC and the compressive recovery RC. In the measurement, the thickness variation was obtained by (T0-Tm) and the compressibility was obtained by {(T0-Tm)/T0}×100(%).

As shown in Table 1, the individual compression workloads WC of the resin films shown in FIGS. 7, 8 and 9 are greater than 0.1 (N·m/m²). The compressibility is greater in the apertured film of FIG. 7 than in the apertured film of FIG. 9 than in the apertured film of FIG. 8. The thickness variation is also greater in the apertured film of FIG. 8 than in the apertured film of FIG. 7 and greater in the apertured film of FIG. 9 than in the apertured film of FIG. 8.

Accordingly, the liquid passage layer 4 may be obtained by using the apertured film of FIG. 7 for the first passage layer 10 and using the apertured film of FIG. 8 or 9 for the second passage layer 20 or by using the apertured film of FIG. 8 for the first passage layer 10 and using the apertured film of FIG. 9 for the second passage layer 20.

TABLE 1

|  |  | FIG. 7 | FIG. 8 | FIG. 9 |
| --- | --- | --- | --- | --- |
| Basis Weight | g/m² | 23 | 25 | 28 |
| Opening Diameter | mm | 0.42/0.32 | 0.64/0.55 | 1.3/1.0 |
| Percent Open Area | % | 18 | 32 | 10 |
| KES (Compression Test) |  |  |  |  |
| Compression Workload (N·m/m²) |  | 0.153 | 0.323 | 1.547 |
| Compressive Recovery (%) |  | 43.44 | 52.08 | 37.88 |
| Initial Thickness (mm) |  | 0.454 | 0.565 | 1.247 |
| Thickness under Load (mm) |  | 0.355 | 0.382 | 0.610 |
| Thickness Variation (mm) |  | 0.099 | 0.183 | 0.637 |
| Compressibility |  | 0.218 | 0.324 | 0.511 |

Therefore, a sanitary napkin according to one embodiment of the present invention may be constructed as follows.

(1) Liquid Passage Layer 4

The first passage layer 10 is made of the resin film of FIG. 7 and the second passage layer 20 is made of the resin film of FIG. 8.

(2) Liquid Absorbent Layer 3

A mixture of fluff pulp and polyacrylic acid salt-based superabsorbent polymer is wrapped in a tissue having a basis weight of 15 g/m² and an air-laid pulp having a weight of 45 g/m² is laid on and bonded to an underside surface intended to face the backsheet 2. The total weight inside the main absorbent region 7 is in the range of 200 to 300 g/m² and the total weight outside the main absorbent region 7 is in the range of 150 to 200 g/m². The region outside the main absorbent region 7 is compressed under heat.

(3) Backsheet 2

A polyethylene resin film having a basis weight of 23.5 g/m² is used for the backsheet.

(4) Construction of Sanitary Napkin

The first and second passage layers 10, 20 are bonded together through a hot-melt type adhesive applied in an amount of 7 g/m². The liquid passage layer 4, which is constructed of the first and second passage layers 10, 20, and the liquid absorbent layer 3 are bonded together through a hot-melt type adhesive, the backsheet 2 is further bonded thereto, and then the compressed grooves 6 are formed in the patter of FIG. 1.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An absorbent article comprising:
a liquid absorbent layer for absorption and retention of liquid; and
a liquid passage layer located on a liquid-receiving side of the liquid absorbent layer, the liquid passage layer including:
a first passage layer; and
a second passage layer disposed between the first passage layer and the liquid absorbent layer, the first passage layer and the second passage layer being resin films formed with a plurality of liquid passage apertures,
each liquid passage aperture being defined by a peripheral wall projecting toward the liquid absorbent layer to provide the first passage layer and the second passage layer with thicknesses greater than a thickness of the resin film itself, the thickness of the first passage layer being the height of the peripheral wall in the first passage layer and the thickness of the second passage layer being the height of the peripheral wall in the second passage layer, and
wherein under a load in a thickness direction, the second passage layer has a greater thickness variation than the first passage layer and
wherein a percent open area for the second passage layer is greater than a percent open area for the first passage layer, where percent open area is determined as the ratio of a surface area open to the plurality of liquid passage apertures in the passage layer to a total surface area for the passage layer;
wherein material forming the resin film of the second passage layer is softer than the material forming the resin film of the first passage layer and
wherein the first passage layer is made of HDPE or MDPE and the second passage layer is made of LLDPE or LDPE.

2. The sanitary napkin of claim 1, wherein when the individual first and second passage layers are under a load in a thickness direction, the second passage layer has a greater compression workload than the first passage layer.

3. The sanitary napkin of claim 2, wherein the first passage layer has a compression workload equal to or greater than 0.1 Nm/m$^2$.

4. The sanitary napkin of claim 2, wherein the thickness of the second passage layer is greater than the thickness of the first passage layer.

5. The sanitary napkin of claim 1, wherein when the individual first and second passage layers are under a load in a thickness direction, the second passage layer has a greater reduction in the open area of the liquid passage aperture than the first passage layer.

6. The sanitary napkin of claim 1, wherein the thickness of the resin film forming the first passage layer is greater than the thickness of the resin film forming the second passage layer.

7. The sanitary napkin of claim 1, wherein liquid passage apertures in the second passage layer each have a peripheral wall that is narrowed to reach a smallest sectional area midway in the thickness direction.

8. The sanitary napkin of claim 1, wherein liquid passage apertures in the second passage layer each have a peripheral wall that is gradually narrowed in the thickness direction along an aperture axis that is directed obliquely to the thickness direction of the second passage layer.

9. The sanitary napkin of claim 8, wherein each liquid passage aperture is bifurcated, having first and second peripheral walls gradually narrowed in the thickness direction respectively along first and second aperture axes directed obliquely to the thickness direction of the second passage layer.

10. The sanitary napkin of claim 1, wherein liquid passage apertures in the second passage layer are each formed with a peripheral wall that is gradually narrowed in the thickness direction of the second passage layer and that has a plurality of cuts also extending in the thickness direction.

11. The sanitary napkin of claim 1, wherein under a load in a thickness direction, the height of the peripheral wall in the second passage layer decreases at a rate greater than a rate of decrease of the height of the peripheral wall in the first passage layer.

12. The sanitary napkin of claim 11, wherein under a predetermined load applied in a thickness direction, the second passage layer has a greater compressibility than the first passage layer and the peripheral wall in the first passage layer is more resistant to crushing as compared to the peripheral wall in the second passage layer.

* * * * *